(12) United States Patent
Rai et al.

(10) Patent No.: US 7,470,796 B2
(45) Date of Patent: *Dec. 30, 2008

(54) METHODS FOR PRODUCING AND PURIFYING 2-HYDROCARBYL-3,3-BIS(4-HYDROXYARYL)PHTHALIMIDINE MONOMERS AND POLYCARBONATES DERIVED THEREFROM

(75) Inventors: Vinod Kumar Rai, Bangalore (IN); Radhakrishna Srinivasarao Arakali, Karnatakazip (IN)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/541,002

(22) Filed: Sep. 29, 2006

(65) Prior Publication Data

US 2007/0055025 A1 Mar. 8, 2007

Related U.S. Application Data

(62) Division of application No. 10/878,757, filed on Jun. 28, 2004, now Pat. No. 7,135,577.

(51) Int. Cl.
*C07D 209/46* (2006.01)
(52) U.S. Cl. ...................................... 548/472
(58) Field of Classification Search ................... 548/472
See application file for complete search history.

(56) References Cited

U.S. PATENT DOCUMENTS

| 4,134,936 A | 1/1979 | Byrne et al. ................. 260/860 |
| 4,217,438 A | 8/1980 | Brunelle et al. |
| 5,204,394 A | 4/1993 | Gosens et al. |
| 5,322,528 A | 6/1994 | Lu-Dai Sung et al. .......... 44/336 |
| 5,344,910 A | 9/1994 | Sybert ......................... 528/201 |
| 5,387,629 A | 2/1995 | McGrath et al. ............. 524/190 |
| 5,455,310 A | 10/1995 | Hoover et al. ............... 525/431 |
| 2005/0222334 A1 | 10/2005 | Srinivasan et al. ........... 525/178 |

FOREIGN PATENT DOCUMENTS

| EP | 1582549 A1 | 10/2005 |
| WO | WO 02/50185 A2 | 6/2002 |

OTHER PUBLICATIONS

Vogel, Practical Organic Chemistry, 3rd Ed. (1956) including pp. 770-775.*
Salazkin et al. Producing Card Biophenols and Some Derivatives Thereof.
Lin and Pearce, Journal of Polymer Science: Polymer Chemistry Edition, (1981) vol. 19, pp. 2659-2670.
Japanese Patent No. JP 03-070790; Publication Date: Mar. 26, 1991; Abstract Only; 1 page.
Japanese Patent No. JP 06-003838; Publication Date: Jan. 14, 1994; Abstract Only; 1 page.
Japanese Patent No. JP 2820277 B2; Publication Date: Nov. 5, 1998; Machine Translation; 22 pages.
Lin et al., "Thermal Degradation Study of Phenolphthalein Polycarbonate", Journal of Polymer Science, Polymer Chemistry Edition, vol. 19, (1981), pp. 2773-2797.
Joag et al., "Effect of Cation Exchange Resin in the Preparation of Phenolphthalein", Indian Journal of Technology, vol. 26, (1998) pp. 491-494.
International Search Report; International Application No. PCT/US2006/047417; International Filing Date Dec. 12, 2006; Date of Mailing of the International Search Report Jul. 5, 2007; 4 pages.
Written Opinion of the International Searching Authority; International Application No. PCT/US2006/047417; International Filing Date Dec. 12, 2006; 3 pages.

* cited by examiner

*Primary Examiner*—Kamal A Saeed
*Assistant Examiner*—Robert Havlin

(57) ABSTRACT

Disclosed herein is a method for producing a 2-hydrocarbyl-3,3-bis(4-hydroxyaryl)phthalimidine. The method comprises forming a reaction mixture comprising at least one substituted or unsubstituted phenolphthalein compound, at least one substituted or unsubstituted primary hydrocarbyl amine, and an acid catalyst; and heating the reaction mixture to form 2-hydrocarbyl-3,3-bis(4-hydroxyaryl)phthalimidine. An adduct of the 2-hydrocarbyl-3,3-bis(4-hydroxyaryl)phthalimidine is formed either by using an excess of the primary hydrocarbyl amine in the first heating step, or by isolating crude 2-hydrocarbyl-3,3-bis(4-hydroxyaryl)phthalimidine after the heating step and then reacting with a further amount of the primary hydrocarbyl amine. The 2-hydrocarbyl-3,3-bis(4-hydroxyaryl)phthalimidine has a formula:

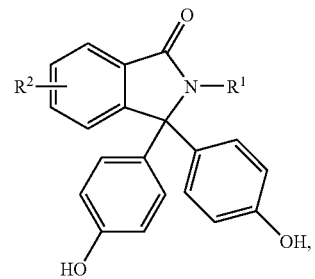

where $R^1$ is selected from the group consisting of a hydrogen and a hydrocarbyl group, and $R^2$ is selected from the group consisting of a hydrogen, a hydrocarbyl group, and a halogen.

24 Claims, 3 Drawing Sheets

FIG. 2

METHODS FOR PRODUCING AND PURIFYING 2-HYDROCARBYL-3,3-BIS(4-HYDROXYARYL)PHTHALIMIDINE MONOMERS AND POLYCARBONATES DERIVED THEREFROM

CROSS REFERENCE TO RELATED APPLICATIONS

This application is a divisional of U.S. patent application Ser. No. 10/878,757 filed Jun. 28, 2004 now U.S. Pat. No. 7,135,577, which is fully incorporated herein by reference.

BACKGROUND

The present disclosure generally relates to methods for producing and purifying 2-hydrocarbyl-3,3-bis(4-hydroxyaryl)phthalimidine monomers (hereinafter sometimes referred to as phenolphthalein derivatives), and polycarbonates as well as other polymers derived utilizing the monomers.

3,3-Bis-(4-hydroxy-phenyl)-3H-isobenzofuran-1-one (hereinafter referred to as phenolphthalein) has been used as an aromatic dihydroxy compound monomer for preparing polycarbonates, which are generally characterized with excellent ductility and high glass transition temperatures. Certain derivatives of phenolphthalein have also been used as aromatic dihydroxy compound monomers to prepare polycarbonate resins as well as polyarylate resins. For example, polycarbonate homopolymers have been prepared by an interfacial polycondensation method using phosgene and (phenolphthalein derivative) monomers such as 3,3-bis(4-hydroxyphenyl)phthalimidine and 2-phenyl-3,3-bis(4-hydroxyphenyl)phthalimidine (hereinafter sometimes referred to as "PPPBP").

Lin and Pearce (Journal of Polymer Science: Polymer Chemistry Edition, (1981) Vol. 19, pp. 2659-2670) reported the synthesis of PPPBP for preparing polycarbonates and other polymers by refluxing phenolphthalein and aniline hydrochloride in aniline for 6 hours, followed by recrystallization from ethanol. During this reaction, side products are created which, if not removed, can result in PPPBP having an unacceptable purity for use as a monomer or as a comonomer in subsequent polymerization reactions. Furthermore, the impurities in the PPPBP monomer include, for example, trace (parts per million) levels of phenolphthalein or phenolphthalein residues that can undesirably produce discoloration in the polycarbonates and other polymers derived therefrom, thereby affecting the transparency of the polymer product. Coloration is not a desirable attribute for many commercial applications. U.S. Pat. No. 5,344,910 discloses that copolymers of PPPBP were found to have poor melt stability resulting in foamy polymer melts and moldings, and discoloration of the resin during melt processing.

It would therefore be desirable to develop a process for improving the purity of phenolphthalein derivatives such as 2-hydrocarbyl-3,3-bis(4-hydroxyaryl)phthalimidine, which can then be used for producing polycarbonates and other polymers having improved properties, such as lower visual coloration and a higher weight average molecular weight.

BRIEF SUMMARY

Disclosed herein is a method for producing phenolphthalein derivatives (for example 2-hydrocarbyl-3,3-bis(4-hydroxyaryl)phthalimidine). The method comprises, heating a reaction mixture comprising a phenolphthalein compound and a primary hydrocarbyl amine, in the presence of an acid catalyst, to form the phenolphthalein derivative product. The method further comprises forming an adduct of the phenolphthalein derivative. The adduct can be formed either (i) by using an excess of the hydrocarbyl amine to cause in situ formation of the an adduct comprising phenolphthalein derivative product and primary hydrocarbyl amine or (ii) by first isolating the crude phenolphthalein derivative product and then further reacting with an additional amount of primary hydrocarbyl amine to form the adduct. The adduct is then precipitated. Finally the adduct is decomposed to produce the 2-hydrocarbyl-3,3-bis(4-hydroxyaryl)phthalimidine.

In another embodiment there is disclosed a method for producing 2-hydrocarbyl-3,3-bis(4-hydroxyphenyl)phthalimidine, comprising heating a reaction mixture comprising a phenolphthalein compound, a primary aromatic amine, and optionally a hydrogen chloride fluid, to form an adduct, neutralizing mixture with sodium bicarbonate, precipitating said adduct of the 2-hydrocarbyl-3,3-bis(4-hydroxyphenyl)phthalimidine and the primary aromatic amine by adding an aromatic hydrocarbon to the reaction mixture and heating said adduct with an alcohol to produce said 2-hydrocarbyl-3,3-bis(4-hydroxyphenyl)phthalimidine.

In another embodiment is disclosed a method for producing a 2-hydrocarbyl-3,3-bis(4-hydroxyphenyl)phthalimidine, comprising heating a reaction mixture comprising a phenolphthalein compound, a primary aromatic amine, and optionally a hydrogen chloride fluid, to form an adduct, neutralizing said mixture with sodium bicarbonate, precipitating the adduct of the 2-hydrocarbyl-3,3-bis(4-hydroxyphenyl)phthalimidine and the primary aromatic amine by adding an aromatic hydrocarbon to the reaction mixture, dissolving said adduct in an aqueous alkali metal hydroxide solution to provide a first solution, adding an aqueous acid to precipitate the 2-hydrocarbyl-3,3-bis(4-hydroxyphenyl)phthalimidine, and heating said 2-hydrocarbyl-3,3-bis(4-hydroxyphenyl)phthalimidine with an alcohol to produce a purified 2-hydrocarbyl-3,3-bis(4-hydroxyphenyl)phthalimidine.

The above described and other features are exemplified by the following detailed description.

DETAILED DESCRIPTION

For the purposes of this disclosure, the term "hydrocarbyl" is defined herein as a monovalent moiety formed by removing a hydrogen atom from a hydrocarbon. Representative hydrocarbyls are alkyl groups having 1 to 25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; aralkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "aryl" as used herein refers to various forms of aryl groups that have been described hereinabove for the "hydrocarbyl" group.

The present disclosure is generally directed to producing and purifying phenolphthalein derivatives, which are suitable for use as monomers and/or co-monomers for preparing polymers. An exemplary phenolphthalein derivative, a 2-hydrocarbyl-3,3-bis(4-hydroxyaryl)phthalimidine, is of Formula (I):

(I)

wherein $R^1$ is selected from a group consisting of a hydrogen and a hydrocarbyl group, and $R^2$ is selected from the group consisting of a hydrogen, a hydrocarbyl group, and a halogen.

Generally, the 2-hydrocarbyl-3,3-bis(4-hydroxyaryl)phthalimidine of Formula (I) can be prepared by the reaction of a primary hydrocarbyl amine of the formula $R^1$—$NH_2$ such as, for example, an aromatic amine (also referred to herein as "aryl amine"), e.g., an aniline, of formula (II):

(II)

wherein $R^1$ is as defined above and $R^3$ is a hydrocarbon or a hydrocarbyl group; with a phenolphthalein compound of formula (III):

(III)

wherein $R^2$ is as previously defined. An acid catalyst is generally used to facilitate formation of the phthalimidine product.

Suitable acid catalysts that can be used include amine salts of mineral acids. Examples of suitable amines for forming the acid catalysts include primary, secondary, and tertiary amines having any combination of aliphatic and aromatic groups bonded to the amine nitrogen. The mineral acids used for preparing the amine salts may be present in a fluid phase, for example, in a gaseous phase or in a liquid phase or in a combination of the gaseous and liquid phases. Non-limiting examples of mineral acids include hydrogen chloride liquid, hydrogen chloride gas, sulfuric acid, nitric acid, and the like.

Suitable examples of amine salt catalysts include primary, secondary, and tertiary amine hydrochlorides. Hydrochloride salts of primary hydrocarbyl amines such as those amines defined by Formula (II) are preferred since the primary hydrocarbyl amines can be one of the starting materials for preparing the phenolphthalein derivatives of formula (I). In one embodiment, the acid catalyst is introduced as a pre-formed salt of an amine and a mineral acid into the reactor. In another embodiment, the acid catalyst is generated in the reactor by first charging the amine into the reactor, and then adding ⅓ to 1 part by weight of an appropriate mineral acid to phenolphthalein derivative. In another embodiment, the acid catalyst is generated in the reactor by first charging the amine and an appropriate mineral acid into the reactor, and then adding the phenolphthalein derivative. In still another embodiment, 0.1 parts to 0.3 parts by weight of hydrogen chloride gas is introduced into a reactor charged with the amine to form an appropriate amount of the amine hydrochloride catalyst. More hydrochloric acid or more hydrogen chloride gas can also used, but is generally not required. A solvent can optionally be employed to initially form the amine hydrochloride from the primary hydrocarbyl amine. The solvent can then be removed (if desired), and the amine catalyst, e.g., an aryl amine salt, can be added to the reaction mixture.

The reaction of the phenolphthalein compound of Formula (III) with the primary hydrocarbyl amine proceeds by a condensation reaction to form the desired phenolphthalein derivative, e.g., the phthalimidine product of Formula (I). An excess of the primary hydrocarbyl amine over the phenolphthalein derivative may be used to keep the reaction proceeding in a forward direction. The condensation reaction can occur at a temperature of 140° C. to 180° C., or, for example, at a temperature of 140° C. to 170° C., or at a temperature of 140° C. to 150° C.

By way of example, a phenolphthalein compound ($R^2$ is H in formula (III)) was reacted with aniline ($R^3$ is H in formula (II)) in the presence of aniline hydrochloride as the acid catalyst to form 2-phenyl-3,3-bis(4-hydroxyphenyl)phthalimidine (also referred to herein as "PPPBP"), shown structurally in formula (IV), (IV)

As will be discussed in the Example Section, the so-formed PPPBP can be produced at high yields of 60% to 75% and advantageously, can be used to produce polycarbonates lower visual coloration and relatively high weight average molecular weights, e.g., about 3,000 to about 150,000 Daltons as measured by gel permeation chromatography using a polystyrene standard. Moreover, the reaction can result in a decrease in the amount of impurities and unreacted phenolphthalein present in the reaction product, i.e., the PPPBP monomer.

Isolation of the desired phenolphthalein derivative from the reaction mixture can be carried out via adduct formation with the primary hydrocarbyl amine employed in the reaction. As used herein, the term "adduct" is defined as an addition product comprising a phenolphthalein derivative and a primary hydrocarbyl amine at about a 1:2 molar ratio. The phenolphthalein derivatives contemplated include the 2-hydrocarbyl-3,3-bis(4-hydroxyaryl)phthalimidine and 2-hydrocarbyl-3,3-{(4-hydroxyaryl)(2-hydroxyaryl)}phthalimidine compounds. Once formed, the adduct can then be decomposed to obtain the particular 2-hydrocarbyl-3,3-bis(4-hydroxyaryl)phthalimidine, e.g., 2-phenyl-3,3-bis(4-hydroxyphenyl)phthalimidine (PPPBP), with a phenolphthalein content of less than or equal to 1,500 parts per million (ppm) and a purity of 99.5% to 99.9% as determined by high performance liquid chromatography (HPLC) techniques.

In one embodiment, the adduct is prepared by adding a phenolphthalein compound to a reaction mixture comprising the primary hydrocarbyl amine and the acid catalyst, followed by neutralization of the reaction mixture with an alkali metal or alkaline earth metal hydroxide, carbonate, and/or bicarbonate to decompose the acid catalyst. The resulting mixture is then filtered and a water-immiscible aromatic hydrocarbon solvent, is added to the filtrate to precipitate an adduct. The adduct is then further filtered and washed with the aromatic hydrocarbon solvent.

In another embodiment, the adduct may be prepared by first treating the reaction mixture comprising the phenolphthalein derivative, e.g., 2-hydrocarbyl-3,3-bis(4-hydroxyphenyl)phthalimidine, with an alkali metal or alkaline earth metal hydroxide, carbonate, or bicarbonate to decompose the amine salt of mineral acid and the mixture filtered. The filtrate is then treated with an aromatic hydrocarbon solvent to precipitate, for example, the crude 2-hydrocarbyl-3,3-bis(4-hydroxyaryl)phthalimidine solids. The solids are then dissolved in a primary hydrocarbyl amine at an elevated temperature of 130° C. to 185° C. and, cooled to room temperature to precipitate the adduct of phenolphthalein derivative and hydrocarbyl amine. The adduct is then filtered, washed with an aromatic hydrocarbon solvent, and dried to a constant weight. The aromatic hydrocarbon solvent used to precipitate the solids is selected from a group consisting of but not limited to toluene, isomeric xylenes or mixtures thereof, chlorobenzene and mesitylene.

In one embodiment the adduct thus obtained is decomposed using a so-called dissociating solvent. As used herein, the term "dissociating solvent" is defined as a solvent that assists in the decomposition of the adduct to separate primary hydrocarbyl amine from the 2-hydrocarbyl-3,3-bis(4-hydroxyaryl)phthalimidine to provide a purified phenolphthalein derivative. The dissociating solvent comprises a straight chain or branched or cyclic aliphatic alcohol containing from 1 to 8 carbon atoms. Non-limiting examples of suitable aliphatic alcohols include methanol, ethanol, iso-propanol, iso-butanol, n-butanol, tertiary-butanol, n-pentanol, iso-pentanol, mixtures of at least one of the foregoing aliphatic alcohols, and the like. In a particular embodiment, aliphatic monohydric alcohols that are miscible with water, such as methanol, ethanol, and isopropanol, for example, are used. The dissociation is typically effected by suspending the adduct in the dissociating solvent and refluxing the so-formed mixture for about 0.5 hours to about 2 hours, preferably for about 0.75 hours to about 1.5 hours and most preferably for about 1.0 hour to about 1.25 hours, at the end of which the phenolphthalein derivative precipitates out as a solid. The solids are then filtered and dried.

In another embodiment the adduct obtained is dissolved in an aqueous inorganic base comprising an alkali metal or alkaline earth metal hydroxide, carbonate, or bicarbonate to provide a first solution. For example, aqueous sodium hydroxide can be used. Next, the first solution is mixed with an aromatic hydrocarbon solvent that is substantially immiscible with water and allowed to separate to form an aqueous layer and an organic layer. The aqueous layer is then treated with a suitable solid adsorbent that can remove color-forming species present in the solution. In one embodiment, a commercially available activated carbon can be used. Treatment with the activated carbon removes color-forming species present in the solution. Suitable activated carbons include, but are not intended to be limited to, the NORIT series of activated carbon available from Norit Corporation, and those activated carbons commercially available from E. Merck Company.

In addition to functioning as a decolorizing agent, the activated carbon treatment also aids in selectively adsorbing the 2-hydrocarbyl-3-{(4-hydroxyaryl)(2-hydroxyaryl)}phthalimidine isomeric impurity. Thus, one method for purifying a crude 2-hydrocarbyl-3,3-bis(4-hydroxyaryl)phthalimidine product comprises contacting an aqueous base solution of the crude product with the activated carbon and filtering off the carbon to provide a second solution. The second solution may again be treated in the same manner, if desired, to provide further reductions in the levels of the 2-hydrocarbyl-3-{(4-hydroxyaryl)(2-hydroxyaryl)}phthalimidine impurity.

In one embodiment, the step of treating and filtering the first solution is done such that it is effective to reduce an amount of phenolphthalein to less than or equal to 1,500 parts per million relative to an overall weight of the 2-hydrocarbyl-3,3-bis(4-hydroxyaryl)phthalimidine. After treatment with the activated carbon, the resulting mixture is filtered to provide a second solution. The second solution is next treated with an aqueous mineral acid, such as an aqueous solution of hydrochloric acid to precipitate a purified 2-hydrocarbyl-3,3-bis(4-hydroxyaryl)phthalimidine. The product is then purified by suspending in an aliphatic alcohol and refluxing the so-formed mixture for about 0.5 hours to about 2 hours, preferably for about 0.75 hours to about 1.5 hours and most preferably for about 1.0 hour to about 1.25 hours, at the end of which the phenolphthalein derivative precipitates out as a solid. The solids are then filtered and dried. Suitable aliphatic alcohols are those which are defined above as the dissociating solvent.

The general methods described hereinabove can advantageously be applied for preparing PPPBP having less than or equal to 1,500 parts per million (ppm) of phenolphthalein and reduced impurities when compared to PPPBP prepared using prior art processes as outlined in the examples.

The 2-hydrocarbyl-3,3-bis(4-hydroxyaryl)phthalimidines, including the exemplary 2-phenyl-3,3-bis(4-hydroxyphenyl)phthalimidine (PPPBP), are commercially valuable monomers or comonomers for producing a variety of polymers and polymer compositions formed by reactions of the phenolic OH groups of the 2-hydrocarbyl-3,3-bis(4-hydroxyaryl)phthalimidines, for example. Suitable polymers that can be produced are polymers selected from the group consisting of homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, ester carbonate, and carbonate repeat units; and a polyetherketone. A suitable example of a copolymer comprising aromatic ester, estercarbonate, and carbonate repeat units is the copolymer produced by the reaction of a hydroxy-terminated polyester, such as the product of reaction of isophthaloyl chloride, and terephthaloyl chloride with resorcinol, with phosgene and an aromatic dihydroxy compound, such as bisphenol A.

In one embodiment, polycarbonates having desirable properties are synthesized, wherein the polycarbonates include structural units of formula (V):

(V)

which are derived from 2-hydrocarbyl-3,3-bis(4-hydroxyaryl)phthalimidine; wherein $R^1$ and $R^2$ are as described previously; and the C=O structural units are derived from a suitable C=O donor such as phosgene or a carbonic acid diester.

The polycarbonate composition may further comprise structural units derived from at least one other aromatic dihydroxy compound such as is represented by the general formula (VI):

(VI)

wherein each $G^1$ is an independently aromatic group; E is selected from the group consisting of an alkylene group, an alkylidene group, a cycloaliphatic group, a sulfur-containing linkage group, a phosphorus-containing linkage group, an ether linkage group, a carbonyl group, a tertiary nitrogen group, and a silicon-containing linkage group; $R^4$ is a hydrogen or a monovalent hydrocarbon group each; $Y^1$ is independently selected from the groups consisting of a monovalent hydrocarbyl group, an alkenyl group, an allyl group, a halogen, an oxy group and a nitro group; each m is independently a whole number from zero through the number of positions on each respective $G^1$ available for substitution; p is a whole number from zero through the number of positions on E available for substitution; t is a natural number greater than or equal to one; s is either zero or one; and u is a whole number.

Suitable examples of E include cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, and adamantylidene; a sulfur-containing linkage such as sulfide, sulfoxide or sulfone, a phosphorus-containing linkage such as phosphinyl, phosphonyl, an ether linkage, a carbonyl group, a tertiary nitrogen group, and a silicon-containing linkage such as a silane or siloxy linkage.

In the aromatic dihydroxy comonomer compound shown in Formula (VI), when more than one $Y^1$ substituent is present, they may be the same or different. The same holds true for the $R^4$ substituent. Where "s" is zero in formula (VI) and "u" is not zero, the aromatic rings are directly joined with no intervening alkylidene or other bridge. The positions of the hydroxyl groups and $Y^1$ on the aromatic nuclear residues $G^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some embodiments, the parameters "t", "s", and "u" are each one; both $G^1$ radicals are unsubstituted phenylene radicals; and E is an alkylidene group such as isopropylidene. In particular embodiments, both $G^1$ radicals are p-phenylene, although both may be ortho- or meta-phenylene or one ortho- or meta-phenylene and the other para-phenylene.

Some illustrative, non-limiting examples of aromatic dihydroxy compounds of formula (VI) include the dihydroxy-substituted aromatic hydrocarbons disclosed by name or formula (generic or specific) in U.S. Pat. No. 4,217,438. Some particular examples of aromatic dihydroxy compound comonomers include, but are not intended to be limited to, 2,4'-dihydroxydiphenylmethane, bis(2-hydroxyphenyl) methane, bis(4-hydroxyphenyl)methane, bis(4-hydroxy-5-nitrophenyl)methane, bis(4-hydroxy-2,6-dimethyl-3-methoxyphenyl)methane, 1,1-bis(4-hydroxyphenyl)ethane, 1,1-bis(4-hydroxy-2-chlorophenyl)ethane, 2,2-bis(4-hydroxyphenyl)propane (bisphenol A), 2,2-bis(3-chloro-4-hydroxyphenyl)propane, 2,2-bis(3-bromo-4-hydroxyphenyl)propane, 2,2-bis(4-hydroxy-3-methylphenyl)propane, 2,2-bis(4-hydroxy-3-isopropylphenyl)propane, 2,2-bis(3-t-butyl-4-hydroxyphenyl)propane, 2,2-bis(3-phenyl-4-hydroxyphenyl)propane, 2,2-bis(3,5-dichloro-4-hydroxyphenyl)propane, 2,2-bis(3,5-dibromo-4-hydroxyphenyl)propane, 2,2-bis(3,5-dimethyl-4-hydroxyphenyl)propane, 2,2-bis(3-chloro-4-hydroxy-5-methylphenyl)propane, 2,2-bis(3-bromo-4-hydroxy-5-methylphenyl)propane, 2,2-bis(3-chloro-4-hydroxy-5-isopropylphenyl)propane, 2,2-bis(3-bromo-4-hydroxy-5-isopropylphenyl)propane, 2,2-bis(3-t-butyl-5-chloro-4-hydroxyphenyl)propane, 2,2-bis(3-bromo-5-t-butyl-4-hydroxyphenyl)propane, 2,2-bis(3-chloro-5-phenyl-4-hydroxyphenyl)propane, 2,2-bis(3-bromo-5-phenyl-4-hydroxyphenyl)propane, 2,2-bis(3,5-disopropyl-4-hydroxyphenyl)propane, 2,2-bis(3,5-di-t-butyl-4-hydroxyphenyl)propane, 2,2-bis(3,5-diphenyl-4-hydroxyphenyl)propane, 2,2-bis(4-hydroxy-2,3,5,6-tetrachlorophenyl)propane, 2,2-bis(4-hydroxy-2,3,5,6-tetrabromophenyl)propane, 2,2-bis(4-hydroxy-2,3,5,6-tetramethylphenyl)propane, 2,2-bis(2,6-dichloro-3,5-dimethyl-4-hydroxyphenyl)propane, 2,2-bis(2,6-dibromo-3,5-dimethyl-4-hydroxyphenyl)propane, 2,2-bis(4-hydroxy-3-ethylphenyl)propane, 2,2-bis(4-hydroxy-3,5-dimethylphenyl)propane, 2,2-bis(3,5,3',5'-tetrachloro-4,4'-dihydroxyphenyl)propane, bis(4-hydroxyphenyl) cyclohexylmethane, 2,2-bis(4-hydroxyphenyl)-1-phenylpropane, 1,1-bis(4-hydroxyphenyl)cyclohexane, 1,1-bis(3-chloro-4-hydroxyphenyl)cyclohexane, 1,1-bis(3-bromo-4-hydroxyphenyl)cyclohexane, 1,1-bis(4-hydroxy-3-methylphenyl)cyclohexane, 1,1-bis(4-hydroxy-3- isopropylphenyl)cyclohexane, 1,1-bis(3-t-butyl-4-hydroxyphenyl)cyclohexane, 1,1-bis(3-phenyl-4-hydroxyphenyl)cyclohexane, 1,1-bis(3,5-dichloro-4-hydroxyphenyl)cyclohexane, 1,1-bis(3,5-dibromo-4-hydroxyphenyl)cyclohexane, 1,1-bis(4'-hydroxy-3'methylphenyl)cyclohexane (DMBPC), 1,1-bis(3,5-dimethyl-4-hydroxyphenyl)cyclohexane, 4,4'-[1-methyl-4-(1-methyl-ethyl)-1,3-cyclohexandiyl]bisphenol (1,3 BHPM), 4-[1-[3-(4-hydroxyphenyl)-4-methylcyclohexyl]-1-methyl-ethyl]-phenol (2,8 BHPM), 3,8-dihydroxy-5a,10b-diphenylcoumarano-2',3',2,3-coumarane (DCBP), 2-phenyl-3,3-bis(4-hydroxyphenyl)phthalimidine, 1,1-bis(3-chloro-4-hydroxy-5-methylphenyl)cyclohexane, 1,1-bis(3-bromo-4-hydroxy-5-methylphenyl)cyclohexane, 1,1-bis(3-chloro-4-hydroxy-5-isopropylphenyl)cyclohexane, 1,1-bis(3-bromo-4-hydroxy-5-isopropylphenyl)cyclohexane, 1,1-bis(3-t-butyl-5-chloro-4-hydroxyphenyl)cyclohexane, 1,1-bis(3-bromo-5-t-butyl-4-hydroxyphenyl)cyclohexane, 1,1-bis(3-chloro-5-phenyl-4-hydroxyphenyl)cyclohexane, 1,1-bis(3-bromo-5-phenyl-4-hydroxyphenyl)cyclohexane, 1,1-bis(3,5-disopropyl-4-hydroxyphenyl)cyclohexane, 1,1-bis(3,5-di-t-butyl-4-hydroxyphenyl)cyclohexane, 1,1-bis(3,5-diphenyl-4-hydroxyphenyl)cyclohexane, 1,1-bis(4-hydroxy-2,3,5,6-tetrachlorophenyl)cyclohexane, 1,1-bis(4-hydroxy-2,3,5,6-tetrabromophenyl)cyclohexane, 1,1-bis(4-hydroxy-2,3,5,6-tetramethylphenyl)cyclohexane, 1,1-bis(2,6-dichloro-3,5-dimethyl-4-hydroxyphenyl)cyclohexane, 1,1-bis(2,6-dibromo-3,5-dimethyl-4-hydroxyphenyl)cyclohexane, 1,1-bis(4-hydroxyphenyl)-3,3,5-trimethylcyclohexane, 1,1-bis(3-chloro-4-hydroxyphenyl)-3,3,5-trimethylcyclohexane, 1,1-bis(3-bromo-4-hydroxyphenyl)-3,3,5-trimethylcyclohexane, 1,1-bis(4-hydroxy-3-methylphenyl)-3,3,5-trimethylcyclohexane, 1,1-bis(4-hydroxy-3-isopropylphenyl)-3,3,5-trimethylcyclohexane, 1,1-bis(3-t-butyl-4-hydroxyphenyl)-3,3,5-trimethylcyclohexane, 1,1-bis(3-phenyl-4-hydroxyphenyl)-3,3,5-trimethylcyclohexane, 1,1-bis(3,5-dichloro-4-hydroxyphenyl)-3,3,5-trimethylcyclohexane, 1,1-bis(3,5-dibromo-4-hydroxyphenyl)-3,3,5-trimethylcyclohexane, 1,1-bis(3,5-dimethyl-4-hydroxyphenyl)-3,3,5-trimethylcyclohexane, 1,1-bis(3-chloro-4-hydroxy-5-methylphenyl)-3,3,5-trimethylcyclohexane, 1,1-bis(3-bromo-4-hydroxy-5-methylphenyl)-3,3,5-trimethylcyclohexane, 1,1-bis(3-chloro-4-hydroxy-5-isopropylphenyl)-3,3,5-trimethylcyclohexane, 1,1-bis(3-bromo-4-hydroxy-5-isopropylphenyl)-3,3,5-trimethylcyclohexane, 1,1-bis(3-t-butyl-5-chloro-4-hydroxyphenyl)-3,3,5-trimethylcyclohexane, 1,1-bis(3-bromo-5-t-butyl-4-hydroxyphenyl)-3,3,5-trimethylcyclohexane, bis(3-chloro-5-phenyl-4-hydroxyphenyl)-3,3,5-trimethylcyclohexane, 1,1-bis(3-bromo-5-phenyl-4-hydroxyphenyl)-3,3,5-trimethylcyclohexane, 1,1-bis(3,5-disopropyl-4-hydroxyphenyl)-3,3,5-trimethylcyclohexane, 1,1-bis(3,5-di-t-butyl-4-hydroxyphenyl)-3,3,5-trimethylcyclohexane, 1,1-bis(3,5-diphenyl-4-hydroxyphenyl)-3,3,5-trimethylcyclohexane, 1,1-bis(4-hydroxy-2,3,5,6-tetrachlorophenyl)-3,3,5-trimethylcyclohexane, 1,1-bis(4-hydroxy-2,3,5,6-tetrabromophenyl)-3,3,5-trimethylcyclohexane, 1,1-bis(4-hydroxy-2,3,5,6-tetramethylphenyl)-3,3,5-trimethylcyclohexane, 1,1-bis(2,6-dichloro-3,5-dimethyl-4-hydroxyphenyl)-3,3,5-trimethylcyclohexane, 1,1-bis(2,6-dibromo-3,5-dimethyl-4-hydroxyphenyl)-3,3,5-trimethylcyclohexane, 4,4-bis(4-hydroxyphenyl)heptane, 4,4'dihydroxy-1,1-biphenyl, 4,4'-dihydroxy-3,3'-dimethyl-1,1-biphenyl, 4,4'-dihydroxy-3,3'-dioctyl-1,1-biphenyl, 4,4'-(3,3,5-trimethylcyclohexylidene)diphenol, 4,4'-bis(3,5-dimethyl)diphenol, 4,4'-dihydroxydiphenylether, 4,4'-dihydroxydiphenylthioether, 1,3-bis(2-(4-hydroxyphenyl)-2-propyl)benzene, 1,3-bis(2-(4-hydroxy-3-methylphenyl)-2-propyl)benzene, 1,4-bis(2-(4-hydroxyphenyl)-2-propyl) benzene, 1,4-bis(2-(4-hydroxy-3-methylphenyl)-2-propyl) benzene 2,4'-dihydroxyphenyl sulfone, 4,4'-dihydroxydiphenylsulfone (BPS), bis(4-hydroxyphenyl) methane, 2,6-dihydroxy naphthalene, hydroquinone, resorcinol, $C_{1-3}$ alkyl-substituted resorcinols, 3-(4-hydroxyphenyl)-1,1,3-trimethylindan-5-ol, 1-(4-hydroxyphenyl)-1,3,3-trimethylindan-5-ol, and 2,2,2',2'-tetrahydro-3,3,3',3'-tetramethyl-1,1'-spirobi[1H-indene]-6,6'-diol. The most typical aromatic dihydroxy compound is Bisphenol A (BPA).

In some embodiments, an isosorbide comonomer can be used with the 2-hydrocarbyl-3,3-bis(4-hydroxyaryl)phthalimidine monomer or other phenolphthalein derivatives to produce polycarbonate copolymers. Isosorbide, sometimes also called 1,4:3,6-dianhydo-D-glucitol, is a rigid, chemically, and thermally stable aliphatic diol that tends to produce copolymers having higher glass transition temperatures, as compared to comonomer compositions which do not include isosorbide.

The carbonic acid diester described above has the general formula (VII):

$$(ZO)_2C=O \qquad (VII),$$

wherein each Z is independently an unsubstituted or substituted alkyl radical, or an unsubstituted or substituted aryl radical. Suitable examples of carbonic acid diesters include, but are not intended to be limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations of two or more carbonic acid diesters thereof. Diphenyl carbonate is widely used as a carbonic acid diester due to its low cost and ready availability on a commercial scale. If two or more of the carbonic acid diesters listed above are utilized, preferably one of the carbonic acid diesters is diphenyl carbonate. Use of activated aromatic carbonates, as the carbonic acid diester is also contemplated. As used herein, the term "activated aromatic carbonate" is defined as a diaryl carbonate that is more reactive than diphenyl carbonate in a transesterification reaction.

Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl)carbonate, bis(o-formylphenyl)carbonate. Unsymmetrical combinations of these structures, wherein the substitution number and type on A and A' are different, are also contemplated. A preferred structure for the activated aromatic carbonate is an ester-substituted diaryl carbonate having the formula (VIII):

wherein $R^5$ is independently at each occurrence a $C_1$-$C_{20}$ alkyl radical, $C_4$-$C_{20}$ cycloalkyl radical, or $C_4$-$C_{20}$ aromatic radical; $R^6$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and c is independently at each occurrence an integer 0-4. In one embodiment, at least one of the $CO_2R^5$ substituents is preferably attached in an ortho position.

Examples of suitable ester-substituted diaryl carbonates include, but are not limited to, bis(methylsalicyl)carbonate (CAS Registry No. 82091-12-1) (also known as BMSC or bis(o-methoxycarbonylphenyl)carbonate), bis(ethyl salicyl) carbonate, bis(propyl salicyl)carbonate, bis(butylsalicyl)carbonate, bis(benzyl salicyl)carbonate, bis(methyl 4-chlorosalicyl)carbonate and the like. In one embodiment, BMSC can be used in a melt polycarbonate synthesis.

A number of polymerization methods can be used for producing a polymer, such as a homopolycarbonate or a copolycarbonate, comprising structural units derived from a 2-hydrocarbyl-3,3-bis(4-hydroxyaryl)phthalimidine, wherein the 2-hydrocarbyl-3,3-bis(4-hydroxyaryl)phthalimidine comprises less than or equal to about 1,500 parts per million of phenolphthalein and has a purity of 99.5 to 99.9% as obtained from HPLC analysis. Suitable methods for fabricating polycarbonates, for example, include a melt transesterification polymerization method, an interfacial polymerization method, and a bischloroformate polymerization method.

As used herein, the term "structural units derived from" when used in the context of describing the portions of the copolycarbonates derived from the aliphatic diol and the aromatic dihydroxy compounds refers to the fact that both such monomers lose their respective hydrogen atoms upon incorporation in the polymer.

As used herein the term "activated carbonate" refers to a diaryl carbonate which is typically more reactive (either kinetically or thermodynamically) toward aromatic dihydroxy compounds than diphenyl carbonate under identical conditions. Activated carbonates are typically (but not necessarily) substituted diaryl carbonates.

The melt transesterification polymerization method is generally carried out by combining a catalyst and a reactant composition to form a reaction mixture; and mixing the reaction mixture under reactive conditions for a time period effective to produce a polycarbonate product, wherein the reactant composition generally comprises a carbonic acid diester of the formula $(ZO)_2C{=}O$, wherein each Z is independently an unsubstituted or a substituted alkyl radical, or an unsubstituted or a substituted aryl radical and the 2-hydrocarbyl-3,3-bis(4-hydroxyaryl)phthalimidine, wherein the 2-hydrocarbyl-3,3-bis(4-hydroxyaryl)phthalimidine comprises less than or equal to about 1,500 parts per million of phenolphthalein relative to an overall weight of said 2-hydrocarbyl-3,3-bis(4-hydroxyaryl)phthalimidine and said 2-hydrocarbyl-3,3-bis(4-hydroxyaryl)phthalimidine has a purity of 99.5% to 99.9% as determined by HPLC analysis.

During the manufacture of the polycarbonates by the melt transesterification method using the activated or unactivated carbonic acid diester, the amount of the carbonic acid diester can comprise about 0.8 moles to about 1.30 moles, and in some embodiments, about 0.9 moles to about 1.2 moles, based on one mole of the 2-hydrocarbyl-3,3-bis(4-hydroxyaryl)phthalimidine or any combination of the 2-hydrocarbyl-3,3-bis(4-hydroxyaryl)phthalimidine and at least one aromatic dihydroxy comonomer.

Suitable melt transesterification catalysts, i.e., polymerization catalysts, include alkali metal compounds, alkaline earth metal compounds, tetraorganoammonium compounds, tetraorganophosphonium compounds, and combinations comprising at least one of the foregoing catalysts.

Specific examples of alkali metal compounds or alkaline earth metal compounds include organic acid salts, inorganic acid salts, oxides, hydroxides, hydrides, and alcoholates of alkali metals and alkaline earth metals. In one embodiment, the catalyst can be an alkali metal compound of the formula $M_1X_1$, wherein $M_1$ is selected from the group consisting of lithium, sodium, and potassium; and $X_1$ is selected from the group consisting of hydroxide and OAr, wherein Ar is a monovalent aromatic radical.

Examples of suitable alkali metal compounds include, but are not limited to, sodium hydroxide, potassium hydroxide, lithium hydroxide, calcium hydroxide, magnesium hydroxide, sodium bicarbonate, potassium bicarbonate, lithium bicarbonate, sodium carbonate, potassium carbonate, lithium carbonate, sodium acetate, potassium acetate, lithium acetate, lithium stearate, sodium stearate, potassium stearate, lithium hydroxyborate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, and the like.

Specific examples of alkaline earth metal compounds include, but are not limited to, calcium hydroxide, barium hydroxide, magnesium hydroxide, strontium hydroxide, calcium bicarbonate, barium bicarbonate, magnesium bicarbonate, strontium bicarbonate, calcium carbonate, barium carbonate, magnesium carbonate, strontium carbonate, calcium acetate, barium acetate, magnesium acetate, strontium acetate, strontium stearate, and the like.

Exemplary tetraorganoammonium compounds include compounds comprising structure (IX):

wherein $R^7$-$R^{10}$ are independently a $C_1$-$C_{20}$ alkyl radical, $C_4$-$C_{20}$ cycloalkyl radical or a $C_4$-$C_{20}$ aryl radical and $X^-$ is an organic or inorganic anion. Suitable anions ($X^-$) include hydroxide, halide, carboxylate, sulfonate, sulfate, carbonate and bicarbonate. In one embodiment, the transesterification catalyst comprises tetramethyl ammonium hydroxide.

In still other embodiments, the catalyst is a tetraorganophosphonium compound. Exemplary quaternary phosphonium compounds include compounds comprising structure (X):

(X)

wherein $R^7$-$R^{10}$ and $X^-$ are as previously described. Illustrative anions include hydroxide, halide, carboxylate, sulfonate, sulfate, carbonate, and bicarbonate.

Where $X^-$ is a polyvalent anion such as carbonate or sulfate anion, it is understood that the positive and negative charges in structures (IX) and (X) are properly balanced. For example, when $R^7$-$R^{10}$ in structure (IX) are each methyl groups and $X^-$ is carbonate, it is understood that $X^-$ represents ½ ($CO_3^{-2}$) as will be appreciated by those skilled in the art.

Specific examples of tetraorganoammonium compounds and tetraorganophosphonium compounds include, but are not limited to tetramethylammonium hydroxide, tetrabutylammonium hydroxide, tetraethylphosphonium hydroxide, tetrabutylphosphonium acetate, tetrabutylphosphonium hydroxide, and the like.

In one embodiment, the catalyst comprises tetrabutyl phosphonium acetate. In an alternate embodiment, the catalyst comprises a mixture of an alkali metal salt or alkaline earth metal salt with at least one quaternary ammonium compound, at least one quaternary phosphonium compound, or a mixture thereof. For example, the catalyst may be a mixture of sodium hydroxide and tetrabutyl phosphonium acetate. In another embodiment, the catalyst is a mixture of sodium hydroxide and tetramethyl ammonium hydroxide.

In another embodiment, the catalyst comprises an alkaline earth metal salt of an organic acid, an alkali metal salt of an organic acid, or a salt of an organic acid comprising both alkaline earth metal ions and alkali metal ions. Alkali metal and alkaline earth metal salts of organic acids, such as for example, formic acid, acetic acid, stearic acid and ethylenediamine tetraacetic acid can also be used. In one embodiment, the catalyst comprises magnesium disodium ethylenediamine tetraacetate (EDTA magnesium disodium salt).

In yet another embodiment, the catalyst comprises the salt of a non-volatile inorganic acid. By "non-volatile" it is meant that the referenced compounds have no appreciable vapor pressure at ambient temperature and pressure. In particular, these compounds are not volatile at temperatures at which melt polymerizations of polycarbonate are typically conducted. The salts of non-volatile acids are alkali metal salts of phosphites; alkaline earth metal salts of phosphites; alkali metal salts of phosphates; and alkaline earth metal salts of phosphates. Suitable salts of non-volatile acids include $NaH_2PO_3$, $NaH_2PO_4$, $Na_2H_2PO_3$, $KH_2PO_4$, $CsH_2PO_4$, $Cs_2H_2PO_4$, or a mixture thereof. In one embodiment, the transesterification catalyst comprises both the salt of a non-volatile acid and a basic co-catalyst such as an alkali metal hydroxide. This concept is exemplified by the use of a combination of $NaH_2PO_4$ and sodium hydroxide as the transesterification catalyst.

Any of the catalysts disclosed above may be used as combinations of two or more substances. Moreover, the catalyst may be added in a variety of forms. For example, the catalyst may be added as a solid as a powder, or it may be dissolved in a solvent, for example, in water or alcohol. The total catalyst composition can be about $1\times10^{-7}$ to about $2\times10^{-3}$ moles, and in other embodiments, about $1\times10^{-6}$ to about $4\times10^{-4}$ moles, for each mole of the combination of, for example, the purified PPPBP and the aromatic dihydroxy compound comonomer.

The progress of the polymerization reaction may be monitored by measuring the melt viscosity or the weight average molecular weight of the reaction mixture using techniques known in the art such as gel permeation chromatography. These properties may be measured by taking discreet samples or may be measured on-line. After the desired melt viscosity and/or molecular weight is reached, the final polycarbonate product may be isolated from the reactor in a solid or molten form. It will be appreciated by a person skilled in the art, that the method of making polycarbonates as described in the preceding sections may be made in a batch or a continuous process.

In one embodiment, the aliphatic homopolycarbonate and aliphatic-aromatic copolycarbonate produced with the phenolphthalein derivative may be prepared in an extruder in presence of one or more catalysts, wherein the carbonating agent is an activated aromatic carbonate. The reactants for the polymerization reaction can be fed to the extruder in powder or molten form. In one embodiment, the reactants are dry blended prior to addition to the extruder. The extruder may be equipped with pressure reducing devices (e.g., vents), which serve to remove the activated phenol by-product and thus drive the polymerization reaction toward completion. The molecular weight of the polycarbonate product may be manipulated by controlling, among other factors, the feed rate of the reactants, the type of extruder, the extruder screw design and configuration, the residence time in the extruder, the reaction temperature, and the pressure reducing techniques present on the extruder. The molecular weight of the polycarbonate product may also depend upon the structures of the reactants, such as, activated aromatic carbonate, aliphatic diol, dihydroxy aromatic compound, and the catalyst employed. Many different screw designs and extruder configurations are commercially available that use single screws, double screws, vents, back flight and forward flight zones, seals, side-streams and sizes. One skilled in the art may have to experiment to find the best designs using generally known principals of commercial extruder design. Vented extruders similar to those that are commercially available may also be used.

The process disclosed herein can advantageously be used to prepare, for example, PPPBP homopolycarbonate and copolycarbonates having a weight average molecular weight (Mw) of about 3,000 to about 150,000 Daltons and a glass transition temperature (Tg) of about 80° C. to about 300° C. The number average molecular weights (Mn) of the homopolycarbonate and copolycarbonates can be from about 1,500 to about 75,000 Daltons.

In the interfacial polymerization method, 2-hydrocarbyl-3,3-bis(4-hydroxyaryl)phthalimidine, with or without one or more comonomers, and phosgene are reacted in the presence of an acid acceptor and an aqueous base to produce said polycarbonate. Tertiary amines, such as for example, trialkylamines are preferably used as acid acceptors. An exemplary trialkylamine is triethylamine. Suitable aqueous bases include, for example, the alkali metal hydroxides, such as sodium hydroxide. The interfacial method can be used for producing polycarbonates comprising structural units derived from 2-hydrocarbyl-3,3-bis(4-hydroxyaryl)phthalimidine, and preferably having molecular weights greater than about 50,000, relative to polystyrene standard.

The interfacial method described above can be suitably adapted to produce polycarbonates through the intermediate formation of 2-hydrocarbyl-3,3-bis(4-hydroxyaryl)phthalimidine bischloroformate. This method is sometimes called the bischloroformate polymerization method. In one embodiment, the method comprises reacting a 2-hydrocarbyl-3,3-bis(4-hydroxyaryl)phthalimidine with phosgene in an organic solvent, and then reacting the bischloroformate either with a 2-hydrocarbyl-3,3-bis(4-hydroxyaryl)phthalimidine, or an aromatic dihydroxy compound in the presence of an acid acceptor and an aqueous base to form the polycarbonate.

The interfacial polymerization method and the bischloroformate polymerization method can be carried in a batch or a continuous mode using one or more reactor systems. To carry out the process in a continuous mode, one or more continuous reactors, such as for example, a tubular reactor can be used. In one embodiment, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one end-capping agent, optionally one or more solvents, and at least one catalyst. The end-capped polycarbonate thus formed is continuously removed from the tubular reactor system. The process can be used for preparing end-capped polycarbonate oligomers (generally polycarbonates having a weight average molecular weight of less than or equal to 10,000 daltons) or polymers having a weight average molecular weight of greater than 10,000 daltons. The processes outlined hereinabove can also be suitably adapted, for example, to produce end-capped polycarbonates via the intermediate formation of a mixture comprising a bisphenol monochloroformate or a bisphenol bischloroformate.

In another embodiment, polymer blends comprise the polymers described previously and at least one thermoplastic polymer. The at least one thermoplastic polymer is selected from the group consisting of vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, ABS resins, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, tetrafluoroethylene, polycarbonate-polyorganosiloxane block copolymers, copolymers comprising aromatic ester, estercarbonate, and carbonate repeat units; mixtures, and blends comprising at least one of the foregoing polymers.

The polymers and polymer blends described hereinabove are valuable for producing articles. In one embodiment, an article comprises a polymer comprising structural units derived from a 2-hydrocarbyl-3,3-bis(4-hydroxyaryl)phthalimidine prepared by following the process described above.

Polymers, particularly polycarbonate homopolymers and copolymers comprising structural units derived from the high purity 2-hydrocarbyl-3,3-bis(4-hydroxyaryl)phthalimidine in general, and PPPBP in particular exhibit lower visual coloration. As such, these polycarbonate polymers are useful for producing articles having a number of useful properties, including lower visual color, among others. The polycarbonate homopolymers and copolymers have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. The polycarbonates also have high transparency, as measured by percent light transmission, of greater than or equal to about 85 percent.

The polycarbonates disclosed herein may also be combined with effective amounts of one or more of various types of additives used selected from the group consisting of fillers, fire retardants, drip retardants, antistatic agents, UV stabilizers, heat stabilizers, antioxidants, plasticizers, dyes, pigments, colorants, processing aids, and mixtures thereof. These additives are known in the art, as are their effective levels and methods of incorporation. Effective amounts of the additives vary widely, but they are usually present in an amount up to about 50% or more by weight, based on the weight of the entire composition. Especially preferred additives include hindered phenols, thio compounds and amides derived from various fatty acids. The preferred amounts of these additives generally ranges up to about 2% total combined weight based on the total weight of the composition.

EXAMPLES

In the following examples, molecular weights were measured by gel permeation chromatography using a polystyrene standard. Glass transition temperatures of the polycarbonates were measured by differential scanning calorimetry by heating the sample at the rate of 10° C. to 20° C. per minute under nitrogen. Yellow index was measured using ASTM D1925 test method on plaques of 3 millimeter thickness and on films of 0.2 millimeter thickness. Films were prepared in a petri dish by casting from a solution of 1.1 grams of a polycarbonate in about 10 milliliters of chloroform.

HPLC analysis was generally carried out by using a solution of about 50 milligrams of the sample dissolved in about 10 milliliters of methanol. The HPLC instrument was equipped with a C18 (reverse phase) column maintained at a temperature of 40° C., and an ultraviolet detector capable of detecting components at a wavelength of 230 nanometers. A solvent mixture of methanol and water of varying relative proportions was used. The flow rate was maintained at 1 milliliter per minute. Area percent assay was computed from the area value for each peak detected in the chromatogram divided by the total area from all peaks detected. To measure weight percent assay, calibration curves for PPPBP, and phenolphthalein were first generated. Then the weight percent of a given component in a sample was calculated using these calibration curves.

Adduct composition indicating 2 moles of aniline added to 1 mole of PPPBP, was determined by nuclear magnetic resonance technique. All $^1$H NMR spectra were recorded on a 400 MHz Fourier transform NMR spectrometer at a sample concentration of 25 mg of the adduct in 1 mL of Acetone d6

All melt transesterification polymerizations were carried out using diphenyl carbonate. The catalyst for all of the polymerization runs was prepared by taking appropriate aliquots of a stock solution of aqueous sodium hydroxide and a 25 weight percent aqueous tetramethylammonium hydroxide. Molded articles were prepared by first preparing pellets of the molding compositions using a 25 millimeter ZSK twin-screw extruder, followed by injection molding using a L&T DEMAG 60 molding machine having a clamping capacity of 60 ton, a screw diameter of 25 millimeters, and shot capacity of 58 grams of polystyrene.

Example 1

In this example, an adduct comprised of aniline and PPPBP was prepared, the crude PPPBP product isolated, and then purified.

A mixture of aniline (340 milliliters (ml)) and concentrated HCl (52 ml, 35% concentration) was heated to reflux under stirring. Water was completely removed by forming an azeotrope with aniline (about 20 ml). The mixture was then cooled to 145° C. and phenolphthalein (Formula (III), $R^2$=H)) 80 grams (g) was added. The reaction mixture was maintained at 145° C. for 26 hours under nitrogen. The reaction mixture was then neutralized with sodium bicarbonate (56 g) under stirring at 145° C. for 0.5 hours and the aniline hydrochloride decomposed. Sodium chloride formed during the neutralization and unreacted sodium bicarbonate was filtered off. Toluene (550 ml) was added to the filtrate and the reaction mass cooled to room temperature. The precipitated solids were filtered off and washed with 100 ml of toluene. The wet cake was dried to constant weight at room temperature (24° C.) to get a dry product (i.e., crude adduct) weighing about 139 g. The crude adduct (139 g) was dissolved in sodium hydroxide solution (450 ml, 4% weight by volume in water), heated to 60° C., and toluene (200 ml) was added to this solution. The mixture was stirred and the toluene layer separated from the aqueous layer. The aqueous layer was treated with 8 g activated charcoal, filtered, and washed with water (150 ml). The clear alkaline solution so obtained was neutralized with concentrated HCl (40 ml) in 80 ml of water. The product was filtered off, washed with water to get a neutral pH of about 7, and dried to a constant weight of 74 g at 112° C. The above product (74 g) was then suspended in methanol (360 ml) and refluxed for 1 hr. Solids separated out, which was filtered, washed with methanol (70 ml), and dried to a constant weight of 68.56 g in an oven at 80° C. to provide the final product, which was found by HPLC analysis to have a PPPBP purity of 99.86%. The yield of the isolated product was 69 to 70 percent of theory. The results are shown in Table 1.

Figure 1:
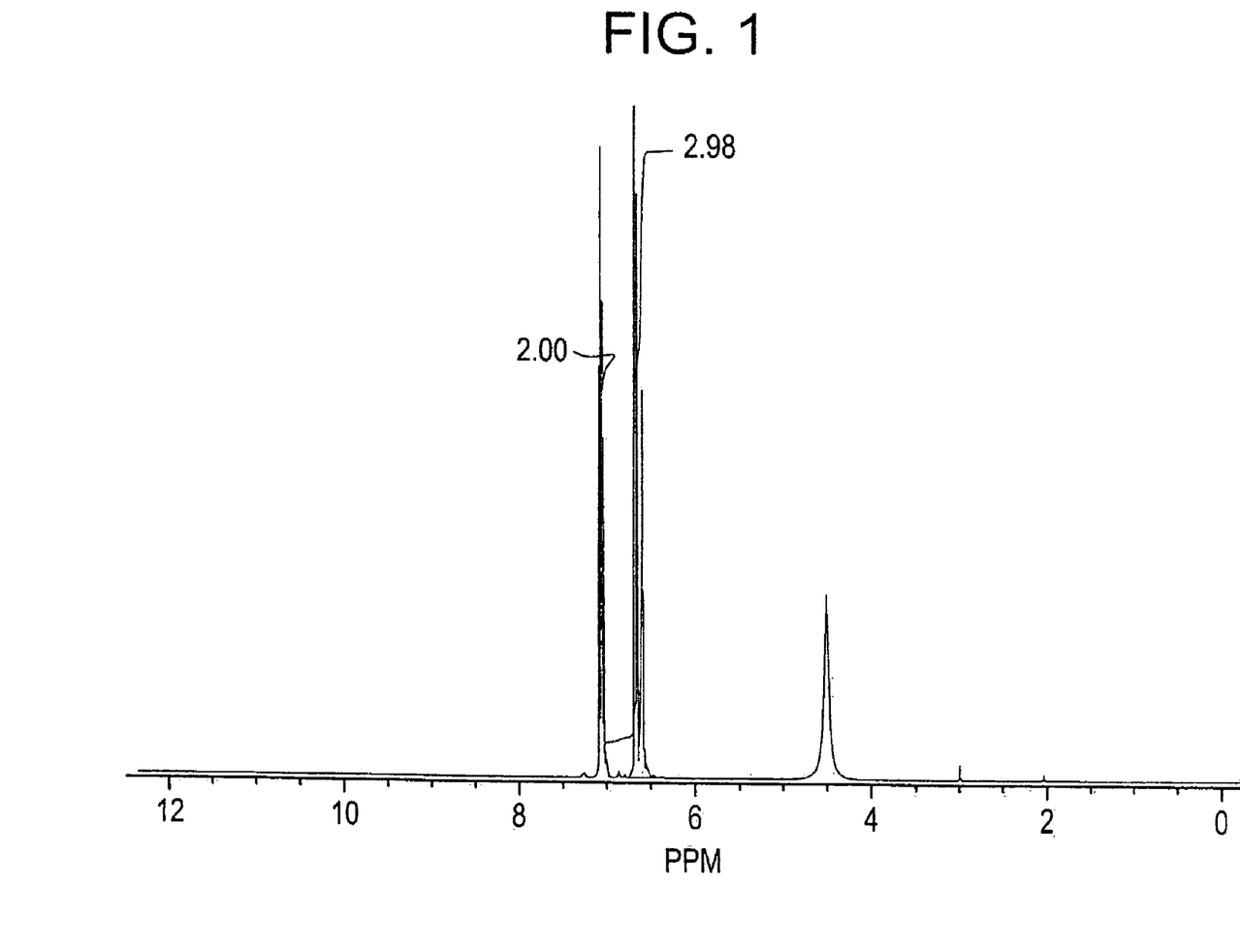
FIG. 1 illustrates the NMR spectra of aniline.
Figure 2:
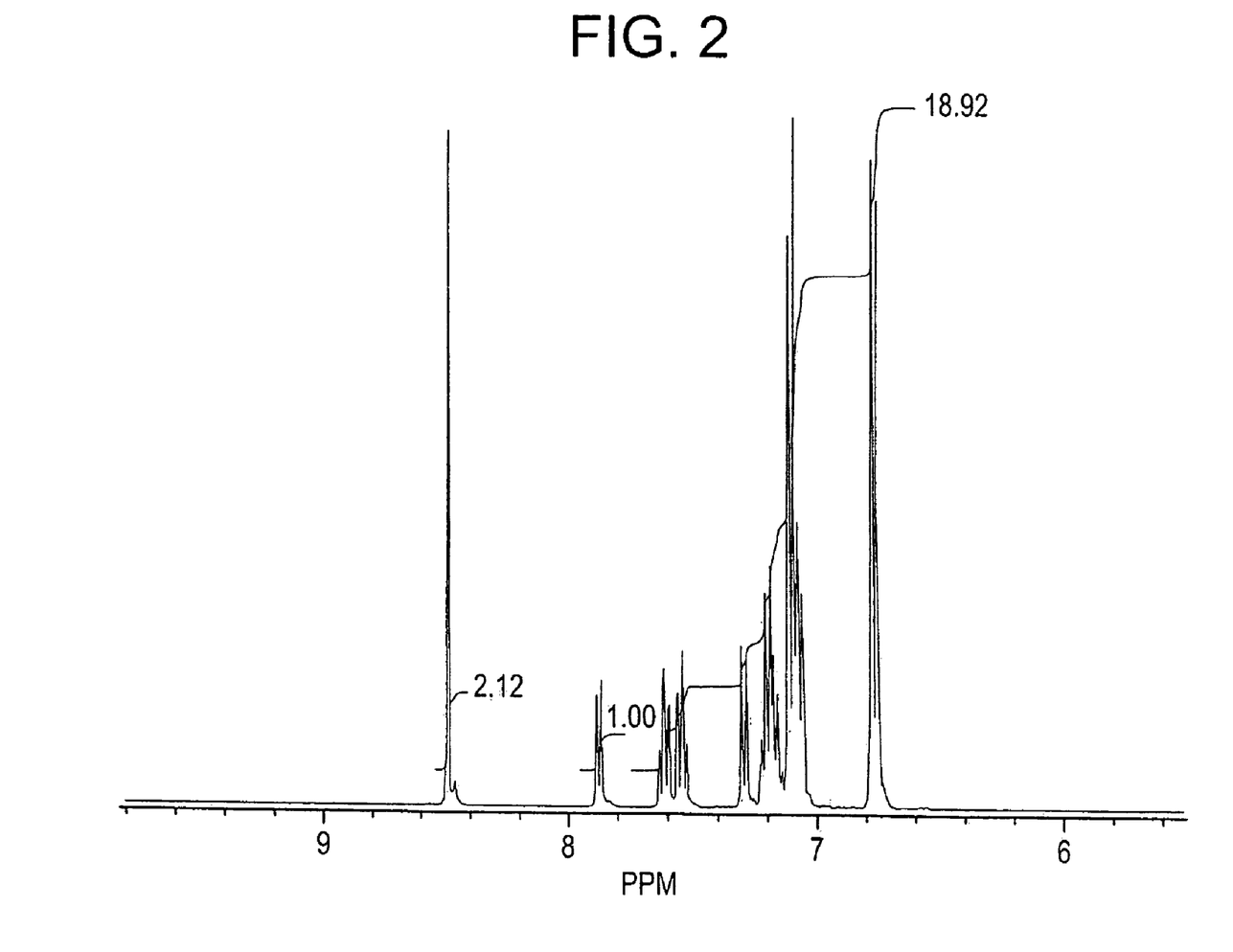
FIG. 2 illustrates the NMR spectra of crude 2-phenyl-3,3-bis(4-hydroxyphenyl)phthalimidine (PPPBP).
Figure 3:
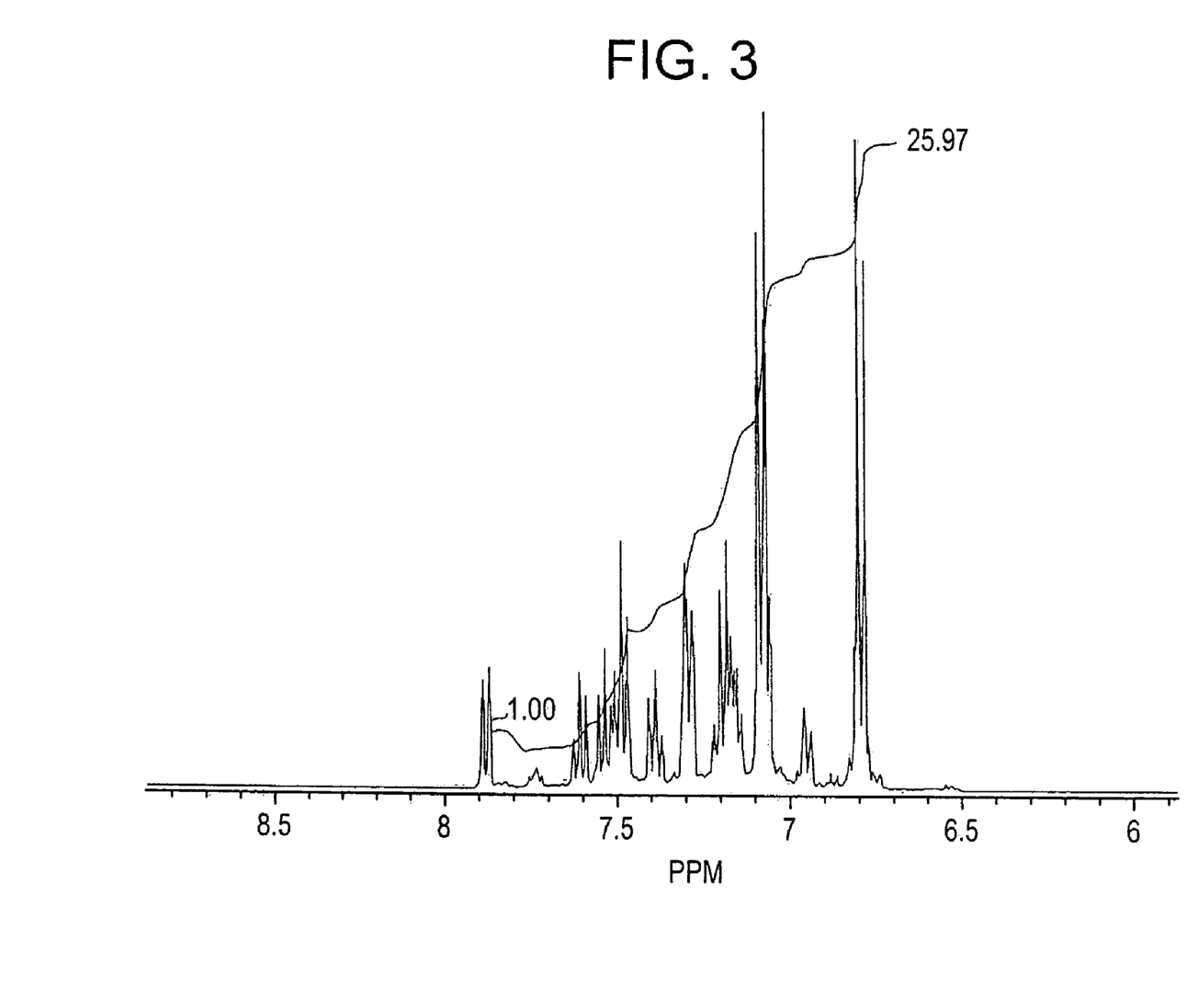
FIG. 3 illustrates the NMR spectra of a PPPBP-aniline adduct.

FIG. 1 illustrates the $^1$H NMR spectra for aniline. The aromatic protons for aniline, i.e., 10 protons, provide signals in the region delta 6.5 to delta 7.15. FIG. 2 illustrates the $^1$H NMR spectra for crude PPPBP. The aromatic protons for PPPBP provide signals in the region delta 6.7 to delta 7.9. FIG. 3 illustrates the $^1$H NMR for PPPBP-Aniline adduct. The signals provided by the aromatic protons of the adduct are at delta 6.7 to 7.95. The signals provided by free aniline in FIG. 1 at delta 6.5 to delta 7.15 are shifted to the region of delta 7.35 to delta 7.65. The chemical shift difference that is observed can be attributed to the deshielding effect for the aniline ring protons because of hydrogen bonding. This may be due the hydrogen bonding between the hydrogen of —OH group of PPPBP & the nitrogen of the —NH2 group of aniline. In addition to this the integration of the 1H proton signals in FIG. 3 accounts for 27 ring protons, which implies 1 mole PPPBP (17 ring protons)+2 moles Aniline (10 ring protons).

Example 2

In this example, the adduct was prepared in accordance with Example 1, wherein the quantity of aniline used was 310 ml. The results are shown in Table 1.

Example 3

In this example, crude phenolphthalein product was firs isolated and then purified via adduct formation.

In this example, a mixture of aniline (133 milliliters (ml)) and concentrated HCl (26 ml, 35% concentration) was heated to reflux under stirring. Water was completely removed by forming an azeotrope with aniline. About 13 ml of aniline distilled over azeotropically with the water. The mixture was then cooled to 145° C. and phenolphthalein 40 grams (g) was added. The reaction mixture was maintained at 145° C. for 25 hours under nitrogen. The reaction mixture was neutralized by adding sodium bicarbonate (28 g) and under stirring at 145° C. for 0.5 hours and the aniline hydrochloride decomposed. Sodium chloride formed in the neutralization reaction and unreacted sodium bicarbonate were filtered off. Toluene (220 ml) was added to the filtrate and the reaction mass cooled to room temperature (24° C.). The precipitated solids were filtered off and washed with 100 ml of toluene and 100 ml of petroleum ether at 60-80° C. The wet cake was dried to constant weight in an oven at 80° C. to provide 49 g of the product, which was found by HPLC analysis to have a PPPBP purity of 97.91% with phenolphthalein 1.76% and an impurity content of 0.18%.

Crude product (45 g) was dissolved in aniline (120 ml) at 150° C. and then cooled to room temperature (24° C.). The product precipitated out after one day. The entire mass was left undisturbed at room temperature for one more day. The solid (adduct) separated was filtered, and washed with 250 ml of toluene to obtain a solid weighing 54 g. The filtrate was left at room temperature for one day and the second crop of solid separated was filtered and washed with 100 ml of toluene to give an additional 10 g of the adduct. The combined adduct 64 g was suspended in 250 ml of methanol refluxed for about thirty minutes, and cooled to room temperature. The solid separated, was filtered, and washed with 100 ml of methanol. Dry weight of the solid was 31.9 g having a purity of 99.87% with 0.12% impurities and undetectable levels of phenolphthalein.

Comparative Example 1

In this example, a prior art process was employed to isolate a PPPBP product.

The prior art process included refluxing a mixture of phenolphthalein (20 grams (g)), aniline hydrochloride (20 g), and 60 ml of aniline at a temperature from about 180° C. to about 185° C. for 5 hours under nitrogen. The dark solution was then stirred into a mixture of 100 grams of ice and 70 grams of concentrated HCl. The violet crystalline colored product was filtered off and washed with water. The crystals were then dissolved in ice-cold 10% sodium hydroxide solution. The solution was treated with 0.2 g active carbon, and then filtered. By drop-wise addition of concentrated HCl into the stirred batch, the color changed to a bright pink, then to a pure white, thick slurry with a pH of 3-4. The precipitated phenolphthalein anilide was then washed neutral with water and dried under vacuum at 70° C. The crude crystals gave a melting point of 288-291° C. with a yield of 79%. Double recrystallization from ethanol, followed by drying the crystals under vacuum at 150° C. gave the product. The results are shown in Table 1.

TABLE 1

| Example | HPLC analysis (Area percent) | | |
|---|---|---|---|
| | PPPBP | Phenolphthalein | Other impurities |
| 1 | 99.8 | 0.1 | 0.05 |
| 2* | 99.8 | 0.03 | 0.06 |
| 3* | 99.8 | <0.03 (undetected) | 0.12 |
| Comparative Example 1 | 97.5 | 0.5 | 2 |

*PPPBP was isolated and then purified by adduct formation.

Table 1 clearly indicates that purification of PPBP by adduct formation provides a significant decrease in the unreacted phenolphthalein and impurities present in the PPPBP product.

Example 5

This Example describes a melt transesterification method for preparing polycarbonate copolymers using 47 weight percent of diphenyl carbonate and 53 weight percent of a monomer mixture consisting of 75 weight percent of BPA and 25 weight percent of the PPPBP prepared in accordance with Examples 1, 2, and Comparative Example 1 The molecular weights of the polycarbonate prepared by this method and the YI of films prepared by solution casting of the polycarbonates are shown in Table 2.

A glass polymerization reactor was passivated by soaking the reactor in a bath containing 1 molar aqueous hydrochloric acid solution. After 24 hours, the reactor was thoroughly rinsed with demineralized water, and finally, with deionized water to ensure that all traces of acid and other contaminants were removed. The reactor was then thoroughly dried and charged with the appropriate amounts of the purified PPPBP monomer or a monomer mixture comprising the purified PPPBP and diphenyl carbonate monomers. The reactor was then mounted in a polymerization assembly and checked to ensure that no leaks were present. The catalyst solutions ($2.5 \times 10^{-4}$ mol of aqueous tetramethylammonium hydroxide and $5 \times 10^{-6}$ mole of aqueous sodium hydroxide), as prepared above, were then introduced into the reactor using a syringe. The atmosphere inside the reactor was then evacuated using a vacuum source and purged with nitrogen. This cycle was repeated 3 times after which the contents of the reactor were heated to melt the monomer mixture. When the temperature of the mixture reached about 180° C. to about 190° C., the stirrer in the reactor was turned on and adjusted to about 40 to about 80 revolutions per minute (rpm) to ensure that the entire solid mass fully melted, a process that usually took about 15 to about 20 minutes. Next, the reaction mixture was heated to a temperature of about 230° C., while the pressure inside the reactor was adjusted to about 170 millibar using a vacuum source. This temperature-pressure-time regime was designated as P1. After stirring the reaction mass at this condition for about 1 hour, the reaction temperature was raised to about 270° C. while readjusting the pressure to around 20 millibar. After being maintained at this condition, designated as P2, for about 30 minutes, the temperature of the reaction mixture was raised to 300° C. while bringing the pressure down to less than or equal to about 1 millibar. After being maintained at this condition, designated as P3, for about 30 minutes, the temperature of the reaction mixture was raised to 300° C. while bringing the pressure down to less than or equal to about 1 millibar. After being maintained at this condition, designated as P4, for about 30 minutes, the temperature of the reaction mixture was raised to about 315° C. while bringing the pressure down to less than or equal to about 1 millibar. After allowing the reaction to proceed under these conditions, designated as P5, for about 10 minutes to about 20 minutes, the pressure inside the reactor was brought to atmospheric pressure and the reactor was vented to relieve any excess pressure. Product isolation was accomplished by breaking the glass nipple at the bottom of the reactor and collecting the material. In the cases where the product was of a very high molecular weight, the hot molten polymer was dropped down by pressurizing the reactor with nitrogen gas.

TABLE 2

| Polycarbonate copolymer prepared from PPPBP of Example # | $M_w$ of polycarbonate (Daltons) |
|---|---|
| Comparative Example | 21,000 |
| Example 1 | 45,976 |
| Example 2 | 46,992 |

Table 2 clearly indicates that improvements in the purity of the phenolphthalein derivative directly impacts molecular weight. A Mw increase of about 2× was observed using PPPBP produced via the adduct formation process described herein.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

The invention claimed is:

1. A method for producing a 2-hydrocarbyl-3,3-bis(4-hydroxyphenyl)phthalimidine of the formula wherein R2 is selected from the group consisting of hydrogen, a halogen, and a hydrocarbyl selected from the group consisting of an alkyl group having 1 to 25 carbon atoms, a cycloalkyl group having 3 to 8 carbon atoms, an aryl group having 6 to 25 carbon atoms, and an arylalkyl group having 7 to 25 carbon atoms, wherein the method comprises:

heating a reaction mixture comprising
 a phenolphthalein compound of the formula:

wherein R² is selected from the group consisting of hydrogen, a halogen, and a hydrocarbyl selected from the group consisting of an alkyl group having 1 to 25 carbon atoms, a cycloalkyl group having 3 to 8 carbon atoms, an aryl group having 6 to 25 carbon atoms, and an arylalkyl group having 7 to 25 carbon atoms,
  a primary aromatic amine of the formula R¹-NH₂, wherein R¹ is an aromatic group having 6 to 25 carbon atoms, and
  hydrogen chloride fluid;
neutralizing the mixture with sodium bicarbonate;
precipitating an adduct of the 2-hydrocarbyl-3,3-bis(4-hydroxyphenyl)phthalimidine and the primary aromatic amine by adding an aromatic hydrocarbon to the neutralized reaction mixture; and
heating the precipitated adduct with an alcohol to produce the 2-hydrocarbyl-3,3-bis(4-hydroxyphenyl)phthalimidine.

2. A method for producing a 2-hydrocarbyl-3,3-bis(4-hydroxyphenyl)phthalimidine of the formula wherein R² is selected from the group consisting of hydrogen, a halogen, and a hydrocarbyl selected from the group consisting of an alkyl group having 1 to 25 carbon atoms, a cycloalkyl group having 3 to 8 carbon atoms, an aryl group having 6 to 25 carbon atoms, and an arylalkyl group having 7 to 25 carbon atoms, wherein the method comprises:
  heating a reaction mixture comprising
    a phenolphthalein compound of the formula:

wherein R² is selected from the group consisting of hydrogen, a halogen, and a hydrocarbyl selected from the group consisting of an alkyl group having 1 to 25 carbon atoms, a cycloalkyl group having 3 to 8 carbon atoms, an aryl group having 6 to 25 carbon atoms, and an arylalkyl group having 7 to 25 carbon atoms,
    a primary aromatic amine of the general formula R¹-NH₂, where R¹ an aromatic group having 6 to 25 carbon atoms, and
    hydrogen chloride fluid;
  neutralizing the heated reaction mixture with sodium bicarbonate;
  precipitating an adduct of the 2-hydrocarbyl-3,3-bis(4-hydroxyphenyl)phthalimidine and the primary aromatic amine by adding an aromatic hydrocarbon to the neutralized reaction mixture;
  dissolving the precipitated adduct in an aqueous alkali metal hydroxide solution to provide a first solution;
  adding an aqueous acid to the first solution to precipitate the 2-hydrocarbyl-3,3-bis(4-hydroxyphenyl)phthalimidine; and
  heating the precipitated 2-hydrocarbyl-3,3-bis(4-hydroxyphenyl)phthalimidine with an alcohol to produce the 2-hydrocarbyl-3,3-bis(4-hydroxyphenyl)phthalimidine.

3. The method of claim 1, wherein the heating of the reaction mixture in conducted at a temperature of 140 to 180° C.

4. The method of claim 1, wherein the heating of the reaction mixture further comprises removing a distillate comprising water.

5. The method of claim 1, wherein the aromatic hydrocarbon comprises a solvent selected from the group consisting of toluene, isomeric xylenes, mixtures of isomeric xylenes, chlorobenzene, and mesitylene.

6. The method of claim 1, wherein the adduct comprises about two moles of the primary amine compound per mole of the phenolphthalein compound.

7. The method of claim 1, wherein the alcohol is an aliphatic alcohol having 1 to 8 carbon atoms.

8. The method of claim 1, wherein the alcohol is methanol, ethanol, or isopropanol.

9. The method of claim 1, wherein the 2-hydrocarbyl-3,3-bis(4-hydroxyphenyl)phthalimidine has a purity of equal to or greater than 99.5 percent as determined by high performance liquid chromatography.

10. The method of claim 1, wherein R² is hydrogen and the primary amine is aniline.

11. The method of claim 10, wherein the 2-hydrocarbyl-3,3-bis(4-hydroxyphenyl)phthalimidine comprises less than or equal to 1,500 parts per million of the phenolphthalein compound, based on the total weight of 2-hydrocarbyl-3,3-bis(4-hydroxyphenyl)phthalimidine.

12. The method of claim 10, wherein the 2-hydrocarbyl-3,3-bis(4-hydroxyphenyl)phthalimidine has a purity of equal to or greater than 99.5 percent as determined by high performance liquid chromatography.

13. The method of claim 2, wherein the heating of the reaction mixture is conducted at a temperature of 140 to 180° C.

14. The method of claim 2, wherein the heating of the reaction mixture further comprises removing a distillate comprising water.

15. The method of claim 2, wherein the aromatic hydrocarbon comprises a solvent selected from the group consisting of toluene, isomeric xylenes, chlorobenzene, and mesitylene.

16. The method of claim 2, wherein the adduct comprises about two moles of the primary amine compound per mole of the phenolphthalein compound.

17. The method of claim 2, wherein the alcohol is an aliphatic alcohol having 1 to 8 carbon atoms.

18. The method of claim 2, wherein the alcohol is methanol, ethanol, or isopropanol.

19. The method of claim 2, wherein the 2-hydrocarbyl-3,3-bis(4-hydroxyphenyl)phthalimidine has a purity of equal to or greater than 99.5 percent as determined by high performance liquid chromatography.

20. The method of claim 2, wherein R² is hydrogen and the primary amine is aniline.

21. The method of claim 20, wherein the 2-hydrocarbyl-3,3-bis(4-hydroxyphenyl)phthalimidine comprises less than or equal to 1,500 parts per million of the phenolphthalein compound, based on the total weight of 2-hydrocarbyl-3,3-bis(4-hydroxyphenyl)phthalimidine.

22. The method of claim 20, wherein the 2-hydrocarbyl-3,3-bis(4-hydroxyphenyl)phthalimidine has a purity of equal to or greater than 99.5 percent as determined by high performance liquid chromatography.

23. The method of claim 1, wherein said 2-hydrocarbyl-3,3-bis(4-hydroxyphenyl)phthalimidine comprises less than or equal to about 1,500 parts per million of the phenolphthalein compound relative to the total weight of said 2-hydrocarbyl-3,3-bis(4-hydroxyphenyl)phthalimidine.

24. The method of claim 2, wherein said 2-hydrocarbyl-3,3-bis(4-hydroxyphenyl)phthalimidine comprises less than or equal to about 1,500 parts per million of the phenolphthalein compound relative to the total weight of said 2-hydrocarbyl-3,3-bis(4-hydroxyphenyl)phthalimidine.

* * * * *